United States Patent
Klassen et al.

(10) Patent No.: US 10,082,461 B2
(45) Date of Patent: Sep. 25, 2018

(54) OPTICAL METROLOGY WITH PURGED REFERENCE CHIP

(71) Applicant: Nanometrics Incorporated, Milpitas, CA (US)

(72) Inventors: Andrew S. Klassen, San Jose, CA (US); Andrew J. Hazelton, San Carlos, CA (US); Andrew H. Barada, Portola Valley, CA (US); Todd M. Petit, Livermore, CA (US); Chuan Sheng Tu, Zhubei (TW)

(73) Assignee: Nanometrics Incorporated, Milpitas, CA (US)

( * ) Notice: Subject to any disclaimer, the term of this patent is extended or adjusted under 35 U.S.C. 154(b) by 232 days.

(21) Appl. No.: 14/809,054

(22) Filed: Jul. 24, 2015

(65) Prior Publication Data

US 2016/0033399 A1 Feb. 4, 2016

Related U.S. Application Data

(60) Provisional application No. 62/030,488, filed on Jul. 29, 2014.

(51) Int. Cl.
*G01N 21/01* (2006.01)
*G01N 21/88* (2006.01)
(Continued)

(52) U.S. Cl.
CPC ......... *G01N 21/4785* (2013.01); *G01N 21/01* (2013.01); *G01N 21/15* (2013.01);
(Continued)

(58) Field of Classification Search
CPC ............... G01N 21/9501; G01N 2201/063
See application file for complete search history.

(56) References Cited

U.S. PATENT DOCUMENTS 4,557,599 A * 12/1985 Zimring ............... G01B 3/02
125/13.01
6,042,651 A 3/2000 Roberson, Jr. et al.
(Continued)

FOREIGN PATENT DOCUMENTS

| JP | 2006128559 A | 5/2006 |
|---|---|---|
| TW | 480612 B | 3/2002 |
| WO | WO2006/055345 A1 | 5/2006 |

OTHER PUBLICATIONS

International Search Report and Written Opinion, PCT/US2015/042308, European Patent Office, dated Jan. 15, 2016, pp. 1-20.
(Continued)

*Primary Examiner* — Shawn Decenzo
*Assistant Examiner* — Jarreas C Underwood
(74) *Attorney, Agent, or Firm* — Silicon Valley Patent Group LLP

(57) ABSTRACT

An integrated metrology module includes a chuck for holding a sample and positioning the sample with respect to an optical metrology device, a reference chip for the optical metrology device, the reference chip being movable to various positions with respect to the optical metrology device, and a reference chip purge device provides a flow of purge gas or air over the reference chip while the reference chip is in the various positions. The reference chip purge device may be static or movable with the reference chip.

16 Claims, 12 Drawing Sheets

(51) Int. Cl.
*G01N 21/94* (2006.01)
*G01N 21/47* (2006.01)
*G01N 21/15* (2006.01)
*G03F 7/20* (2006.01)

(52) U.S. Cl.
CPC ... *G03F 7/70933* (2013.01); *G01N 2021/151* (2013.01); *G01N 2201/02* (2013.01); *G01N 2201/068* (2013.01)

(56) References Cited

U.S. PATENT DOCUMENTS

| | | | |
|---|---|---|---|
| 6,274,878 B1* | 8/2001 | Li | H01L 21/67259 250/222.1 |
| 6,541,376 B2* | 4/2003 | Inada | G03F 7/162 438/618 |
| 6,817,369 B1 | 11/2004 | Riedel et al. | |
| 7,138,640 B1* | 11/2006 | Delgado | G01N 21/15 250/372 |
| 7,342,235 B1 | 3/2008 | Harrison et al. | |
| 7,489,389 B2* | 2/2009 | Shibazaki | G03F 7/70716 355/72 |
| 7,564,552 B2 | 7/2009 | Fielden et al. | |
| 7,755,764 B2* | 7/2010 | Kwak | G01B 11/0625 250/372 |
| 7,981,472 B2* | 7/2011 | Dalton | C23C 16/45544 117/84 |
| 8,092,599 B2* | 1/2012 | Sferlazzo | C23C 16/45589 118/715 |
| 8,216,382 B2* | 7/2012 | Shindo | B08B 7/0042 134/1 |
| 8,334,222 B2* | 12/2012 | Gotou | H01L 21/02049 257/E21.001 |
| 8,830,486 B2* | 9/2014 | Kwak | G01B 11/0641 356/445 |
| 9,257,320 B2* | 2/2016 | Fosnight | H01L 21/67775 |
| 9,851,297 B2* | 12/2017 | Battefeld | G01N 21/51 |
| 2003/0045098 A1 | 3/2003 | Verhaverbeke et al. | |
| 2004/0207838 A1* | 10/2004 | Ebert | G01N 21/01 356/237.4 |
| 2005/0252752 A1 | 11/2005 | Fielden et al. | |
| 2010/0024887 A1* | 2/2010 | Williams | F15D 1/00 137/2 |
| 2010/0124610 A1* | 5/2010 | Aikawa | C23C 16/4584 427/255.28 |
| 2010/0277741 A1 | 11/2010 | Walsh et al. | |
| 2013/0010311 A1 | 1/2013 | Kwak et al. | |

OTHER PUBLICATIONS

Machine Translation in English of Abstract of JP2006128559-A visited at www.espacenet.com on Nov. 4, 2015, 2 pages.
Invitation to Pay Additional Fees dated Oct. 20, 2015 for International Application No. PCT/US2015/042308 filed on Jul. 27, 2015 by Nanometrics Incorporated, 7 pages.

* cited by examiner

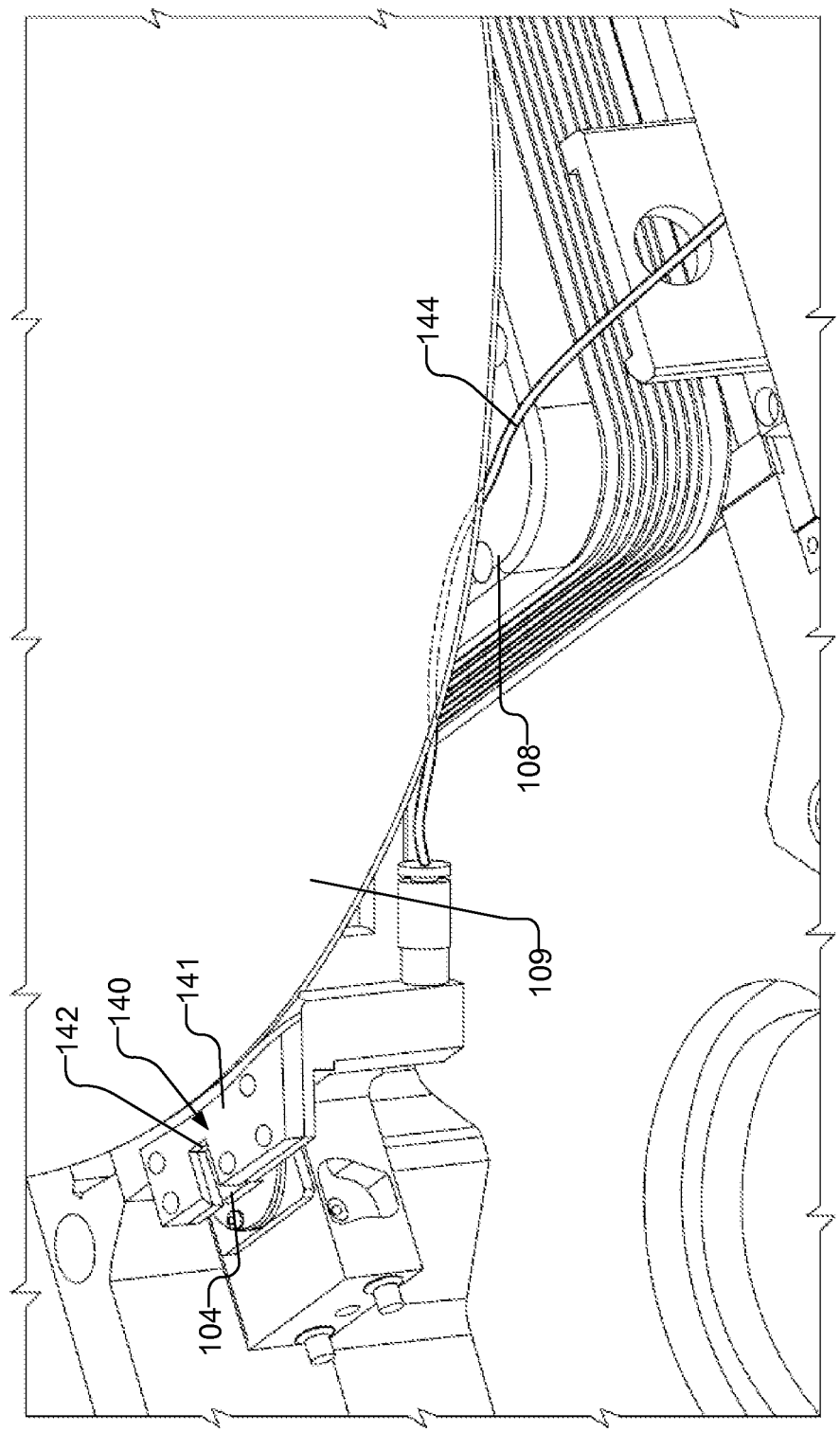

OPTICAL METROLOGY WITH PURGED REFERENCE CHIP

CROSS REFERENCE TO RELATED APPLICATIONS

This application claims priority under 35 USC 119 to U.S. Provisional Application No. 62/030,488, entitled "Optical Metrology With Purged Reference Chip," filed Jul. 29, 2014, which is incorporated herein by reference in its entirety.

BACKGROUND

To improve process control for some semiconductor manufacturing processes, integrated metrology (IM) modules are attached to the process tool and used to measure and quickly provide feedback for real-time control of the process. A typical IM module is built with the same form factor as a loadport, allowing it to be attached to the process tool EFEM (equipment front end module) in place of a loadport. In this case, the wafer handling robot, which is a part of the EFEM, can easily load wafers into the IM module. Typically, there is an open port between the IM and the EFEM, allowing the robot to freely load wafers into the IM.

In order to fit into the form factor of a loadport, the IM needs to be fairly compact. While typical stand-alone metrology tools may have a fan filter unit (FFU) to filter out particles, condition the air temperature, and provide laminar downflow, there is generally not enough space in the IM to include this FFU, so the conditioned air is provided by the EFEM.

In some cases, the metrology device in the IM module may be a spectroscopic reflectometer (SR), but other types of metrology devices may be used. Generally, the spectroscopic reflectometer measures the reflectivity of the wafer across a range of wavelengths. This information can be used to derive, for example, a film thickness of a thin film on the surface of the wafer, or the critical dimension (CD) of a device on the wafer. Reflectivity measurements typically require a reference reflectivity to be measured for calibration. By way of example, the reference reflectivity may be measured on a bare silicon reference chip. The reference chip may be mounted inside the IM chamber, e.g., in close proximity to the wafer.

With the IM module directly connected to the process tool, wafers may be loaded into the IM module immediately after they leave the processing module. Measuring wafers immediately after leaving the processing module allows for rapid process feedback, but in many cases, remnants from the processing are still present on the wafer, which may affect the performance of the metrology device. For example, in the case of an etch process, the etch gases may be absorbed by the processed wafer, and slowly leak out (outgas). For example, in the case of polysilicon etch, bromic acid (hydrogen bromate, $HBrO3$) is sometimes used. When wafers are measured after the etch process, the etch gases may leak out into the environment of the IM module.

The introduction into the metrology environment of process remnants may affect the optical properties of the reference chip. The reference chip is used to calibrate the metrology device, and thus, changes to the optical properties to the reference chip may adversely affect the measurement results. For example, gases that are used to etch silicon during processing, may outgas from the wafer and etch the bare silicon reference chip, thereby changing the surface properties of the reference chip. Other gases used during processing may condense on the surface of the reference chip, which may also change the optical properties of the reference chip.

SUMMARY

An integrated metrology module includes a chuck for holding a sample and positioning the sample with respect to an optical metrology device, a reference chip for the optical metrology device, the reference chip being movable to various positions with respect to the optical metrology device, and a reference chip purge device provides a flow of purge gas or air over the reference chip while the reference chip is in the various positions. The reference chip purge device may be static or movable with the reference chip.

In one implementation, an apparatus includes a chuck for holding a sample and positioning the sample with respect to an optical metrology device; a reference chip for the optical metrology device, the reference chip being movable to various positions with respect to the optical metrology device; and a reference chip purge device that provides a flow of purge gas or air over the reference chip while the reference chip is in the various positions.

In one implementation, an integrated metrology module includes a chuck for holding a sample and moving the sample in a linear direction to position the sample with respect to an optical metrology device; a reference chip for the optical metrology device, the reference chip being mounted to the chuck and movable in the linear direction to various positions with respect to the optical metrology device; and a reference chip purge device comprising a linear purge tube having a plurality of apertures through which purge gas or air is directed over the reference chip while the reference chip is moved in the linear direction.

In one implementation, an integrated metrology module includes a chuck for holding a sample and positioning the sample with respect to an optical metrology device; a reference chip for the optical metrology device, the reference chip being movable to various positions with respect to the optical metrology device; and a reference chip purge device coupled to the chuck and movable with the reference chip to the various positions with respect to the optical metrology device, the reference chip purge device comprising at least one aperture through which purge gas or air is expelled over the reference chip while the reference chip is in the various positions.

BRIEF DESCRIPTION OF THE DRAWINGS

FIGS. 7 and 8 illustrate a side perspective view and side view and perspective view, respectively, of the reference chip and purge system moves with the wafer chuck and reference chip.

DETAILED DESCRIPTION

Figure 1:
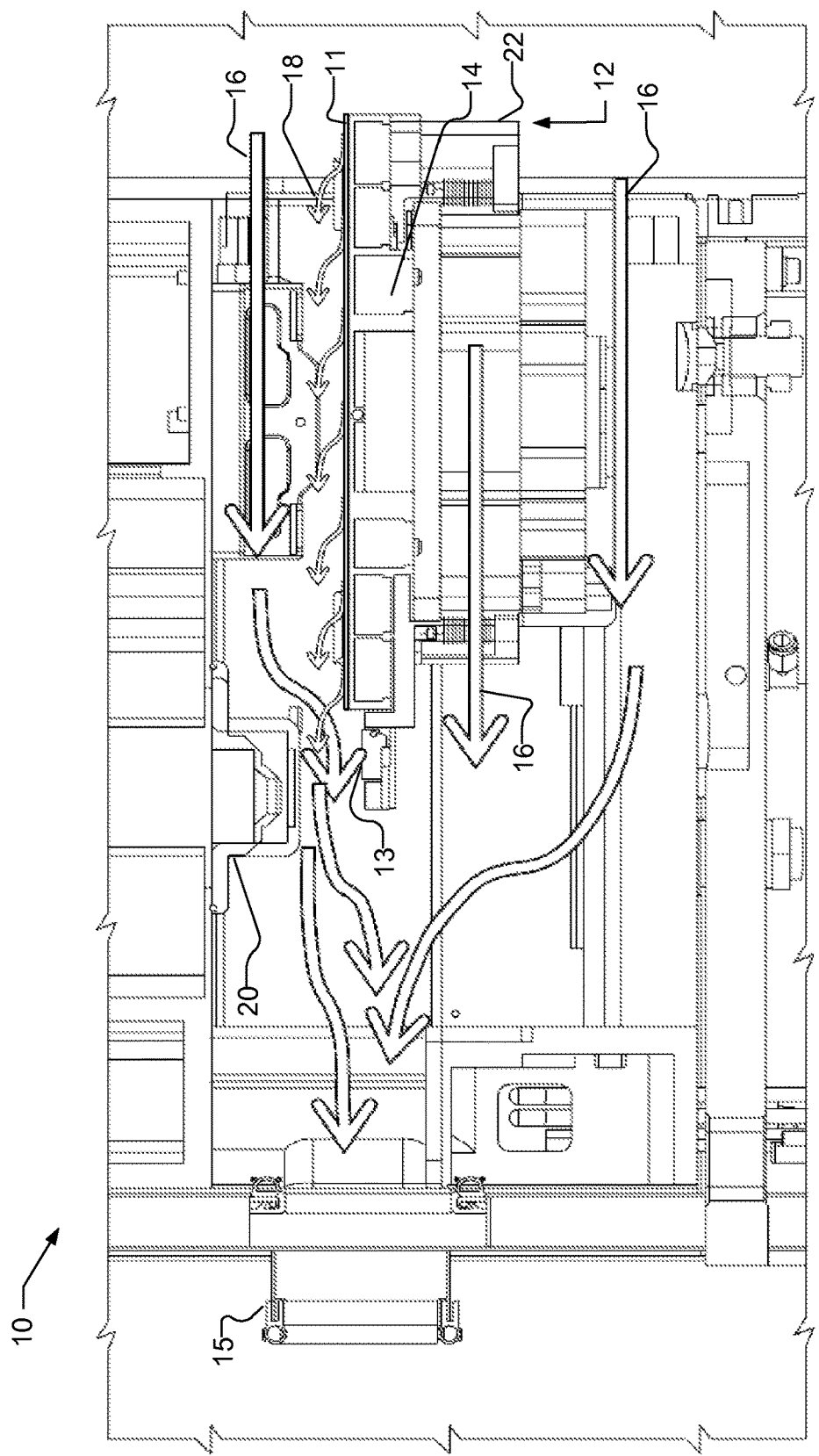
FIG. 1 illustrates a side view of a conventional integrated metrology module showing the typical airflow through the IM module.

FIG. 1 illustrates a side view of a conventional integrated metrology (IM) module 10 showing the typical airflow through the IM module. The IM module 10 is attached to a process tool EFEM (equipment front end module) in place of a loadport. With the IM module 10 directly connected to the process tool 12, wafers can be loaded into the IM module 10 immediately after exiting the process module. The IM module 10 permits measurement of wafers immediately after processing, thereby enabling rapid process feedback. In many cases, however, processing remnants, which may affect the performance of the metrology device, will be present on the wafer when the wafer is loaded into the IM module 10. By way of example, in etch processes, the etch gases, such as bromic acid (hydrogen bromate, HBrO3), may be absorbed in pores of the processed wafer, and may slowly leak out (outgas) from the wafer into the environment of the IM module 10. The process remnants may adversely affect the performance of the metrology device in the IM module 10.

The EFEM, which is not shown in FIG. 1, is on the right side of the IM module 10. During operation, clean air from the EFEM enters the IM module 10 from the right, shown by arrows 16, and flows along the top surface of the wafer 11, and is exhausted through a stage exhaust port 15 in the IM module 10 on the left. There is also air flow alongside and underneath the wafer, also indicated by arrows 16. When a processed wafer 11 is loaded from a processing chamber, e.g., used for etching, onto the chuck 14 of the IM module 10, the wafer 11 may outgas etch gas, e.g. HBrO3, shown by arrows 18, which enters the main air flow path 16 and is also exhausted to the left through the stage exhaust port 15. FIG. 1 also illustrates the reference chip 13. As can be seen in FIG. 1, the clean air 16, as well as the outgas air 18, passes over the reference chip 13 on its way to the stage exhaust port 15.

The reference chip 13 is used to calibrate the metrology device 20. The metrology device 20 may be, e.g., a reflectometer or a spectroscopic reflectometer, discussed below in reference to FIG. 15, or another optical metrology device. Metrology device 20 is sensitive to any changes in the optical properties of the reference chip 13. The introduction of process remnants, such as etch outgas, can affect the optical properties of the reference chip 13. Some process gases, for example, are used to etch silicon, and, thus, may also etch a bare silicon reference chip 13, changing the optical properties of the reference chip 13. Other gases used in processing may condense on the surface of the reference chip 13, also changing the optical property of the reference chip 13. Whether the reference chip 13 is etched or gases condense on the reference chip 13, the change in optical properties of the reference chip 13 may affect the accuracy of measurements produced by the metrology device 20.

As illustrated in FIG. 1, the reference chip 13 may be attached to the chuck 14, which moves the reference chip 13 moves under the metrology device 20 along with the wafer 11. The chuck 14 is coupled to a stage 22 capable of motion in Polar coordinates (i.e., R and θ), and thus, the wafer 11 may be rotated (θ motion) or moved linearly (R motion). As illustrated in FIG. 1, the chuck 14 is shown at the far right extent of its travel. The chuck 14 and stage 22 may move the wafer 11 to the left in FIG. 1, so that the reference chip 13 is close to the stage exhaust port 15. If desired, the stage 22 may move the chuck 14 using Cartesian coordinates. Alternatively, the reference chip 13 may not be attached to the chuck 14 and my move independently from the chuck 14, e.g., with its own actuation. Additionally or alternatively, at least a portion of the metrology device 20, such as the optics, may move to produce relative movement between the wafer 11 and the metrology device 20.

As the reference chip 13 is affected by the introduction of process remnants from the wafer 11, it is desirable to protect the reference chip 13 from process remnants from the wafer 11, such as etch outgas. The reference chip 13 may be protected from process remnants including etch outgas from the wafer 11, by providing a flow of clean gas that purges the area around the surface of the reference chip 13 thereby preventing the process remnants from contacting the reference chip 13. It should be noted that because the reference chip 13 is coupled to the chuck 14, or moves independently from the chuck 14, the reference chip 13 is rarely in the optical path of the metrology device 20. For example, the reference chip 13 is in the optical path of the metrology device 20 only when the reference chip 13 is being sampled by the metrology device 20. Thus, purging the optical path of the metrology device 20 with clean air or gas will not adequately protect the reference chip 13 from the process remnants from the wafer 11.

Figure 2:
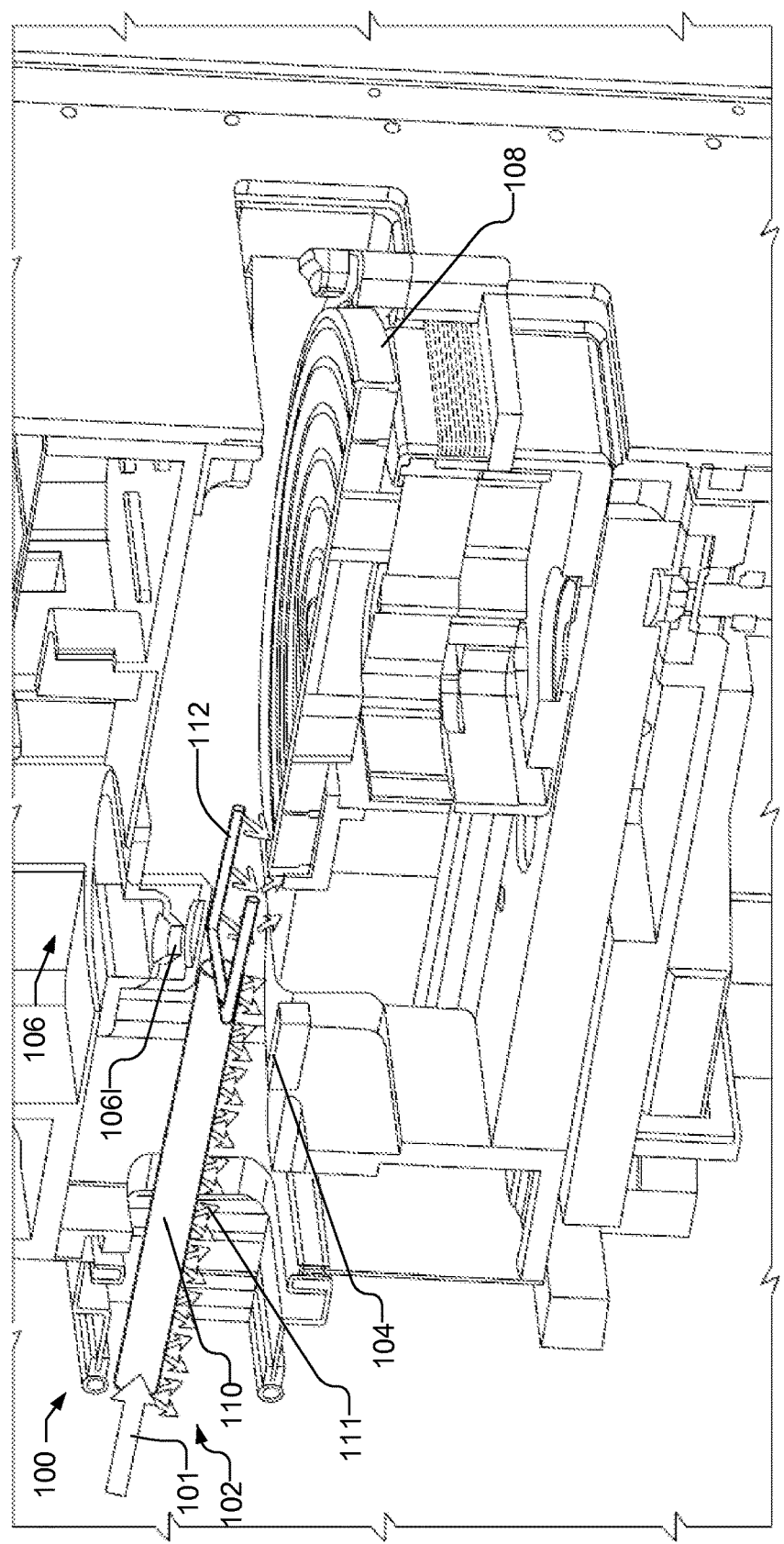
FIGS. 2 and 3 illustrate a side perspective view and side view, respectively, of an integrated metrology module 100 that includes a purge system 102 that provides a constant flow of purging gas to the reference chip 104.
Figure 3:
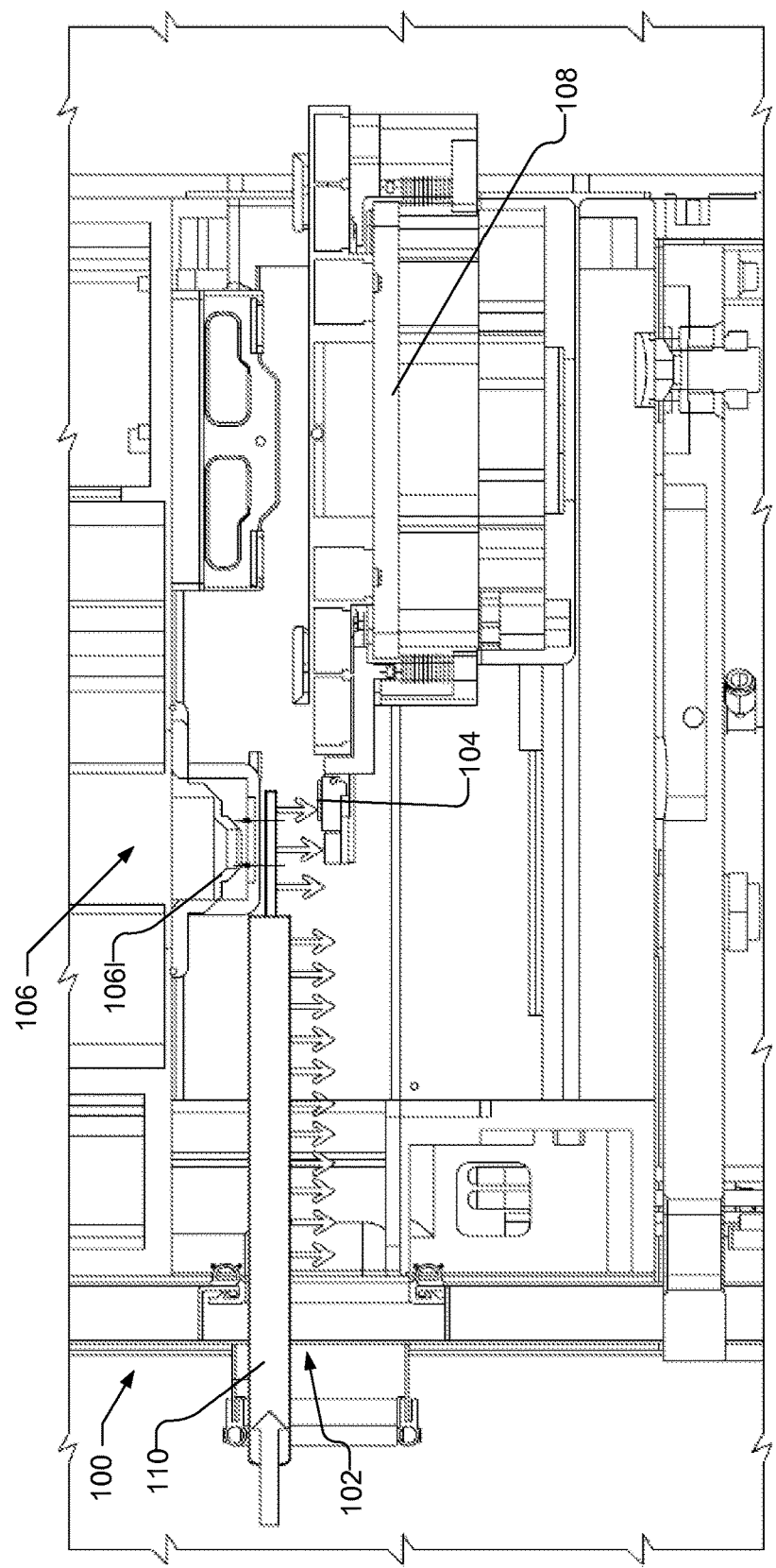

FIG. 2 illustrates a side perspective view of an IM module 100 with a wafer chuck 108 and that is similar to the IM module 10 shown in FIG. 1, but includes a purge system 102 that provides a constant flow of purging gas to a reference chip 104, regardless of the position of the reference chip 104 with respect to the metrology device 106 (only the lens 106l of the metrology device 106 is illustrated in FIG. 2). FIG. 3 illustrates a side view of the IM module 100 with the purge system 102. As illustrated, the purge system 102 includes a large linear purge tube 110 and a plurality of apertures through which purge gas or air is directed (as illustrated by arrows 111) over the reference chip 104 while the reference chip is moved in a linear direction. The linear purge tube 110 is connected to a source of clean purge gas, e.g., clean dry air or nitrogen, (not shown) from the left side of the IM module 100 to receive a supply of purge gas or air (shown by arrow 101). The purge tube 110 extends into the IM module 100 under the lens 106l of the metrology device 106. Under the lens 106l, the purge tube 110 is split into a pair of smaller tubes 112 on either side of the lens 106l of the metrology device 106 so as to not block the lens 106l. The large purge tube 110 may provide a downward air flow, while the pair of smaller tubes 112 provide air flow that is directed diagonally downward. A plurality of apertures in the purge tube 110 along its length, direct a flow of clean air downwards over the reference chip 104 along its entire range of travel. The forced flow of clean purge gas acts to expel the process remnant contaminated air along the full motion path of the reference chip 104. If desired, the pair of smaller tubes 112 may provide a diagonal upward flow of gas to the window (or lens 106l) of the metrology device 106.

Figure 4:
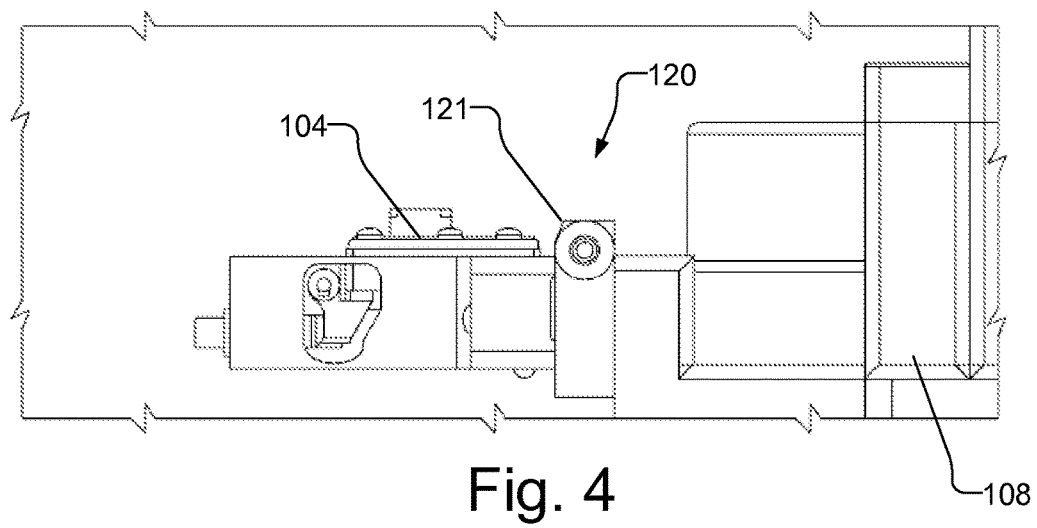
FIGS. 4 and 5 illustrate a side view and front perspective view, respectively, of a wafer chuck with a mounted reference chip and purge system that moves with the wafer chuck and reference chip.
Figure 6:
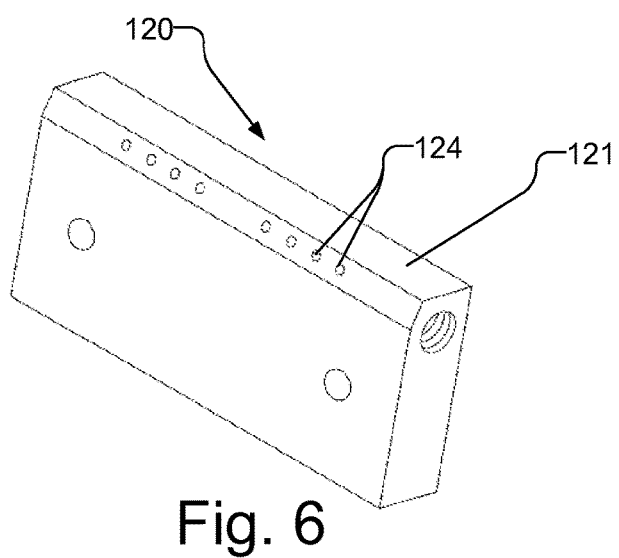
FIG. 6 illustrates a perspective view of the purge system from FIG. 4.
Figure 5:
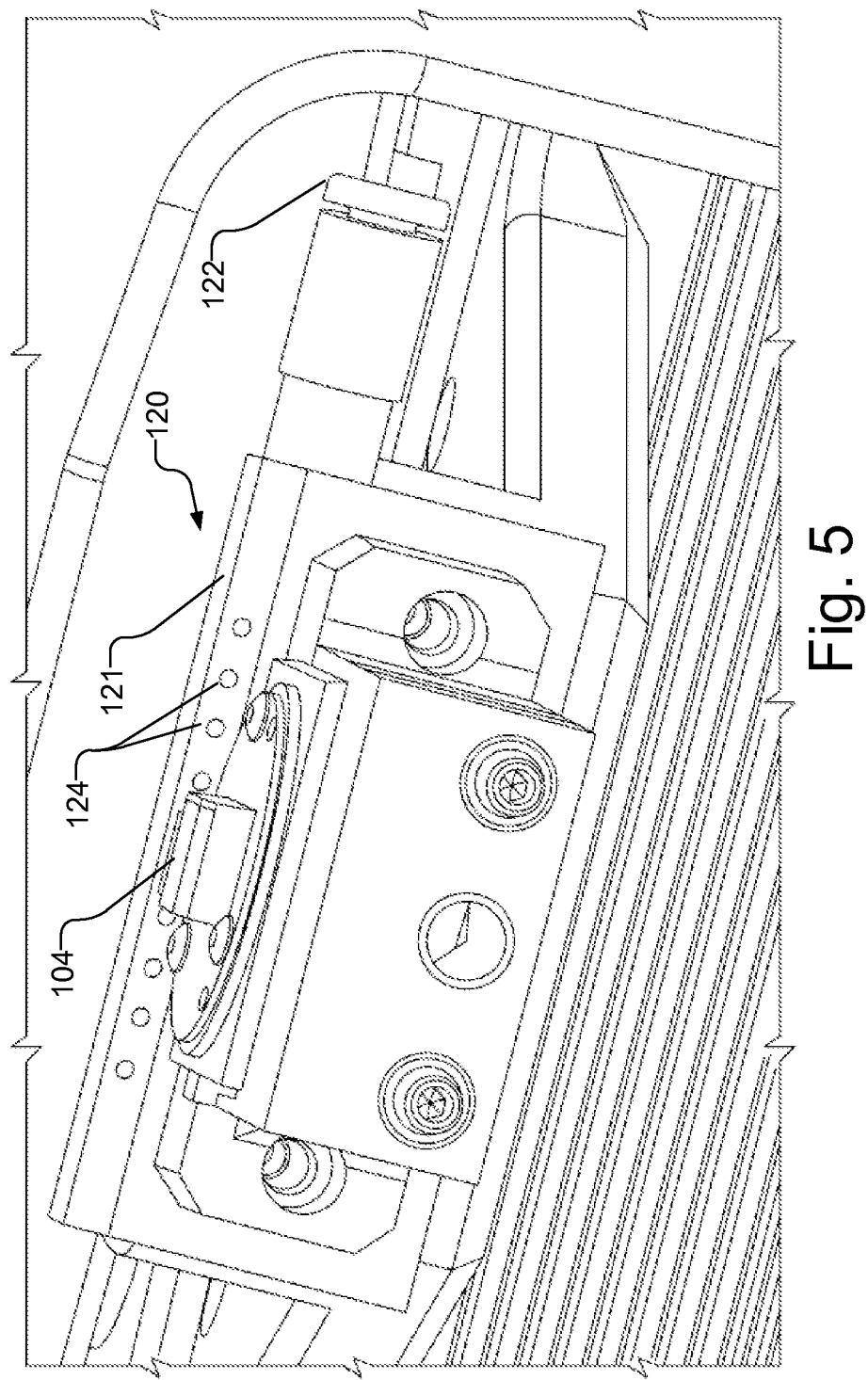

FIG. 4 illustrates a side view of a wafer chuck 108 with a reference chip 104 and purge system 120 mounted to the chuck 108 and movable with the reference chip 104 to various positions with respect to the optical metrology device 106 (shown in FIG. 2), and that may be used with the IM module 100 shown in FIGS. 2 and 3, in place of or in addition to purge system 102. FIG. 5 illustrates a front perspective view of the reference chip 104 and purge system 120 and FIG. 6 illustrates a perspective view of the purge system 120. As illustrated, a purge nozzle 121 is inserted between the reference chip 104 and the wafer chuck 108. By way of example, the purge nozzle 121 may be machined aluminum and, e.g., 7 mm wide. A source of clean purge gas or air is provided at a fitting 122 of the purge nozzle 121, and at least one aperture 124 expels the purge gas or air, which is directed over the reference chip 104. The purge system 120 is coupled to the wafer chuck 108 and accordingly moves with the chuck 108 and a wafer held on the chuck 108. While the purge system 120 requires plumbing within the IM module 100 to provide the clean purge gas, it has the advantage of reducing the quantity of purge gas required and it provides the purge gas more directly to the reference chip 104 than the purge system 102 shown in FIGS. 1 and 2.

Figure 8:
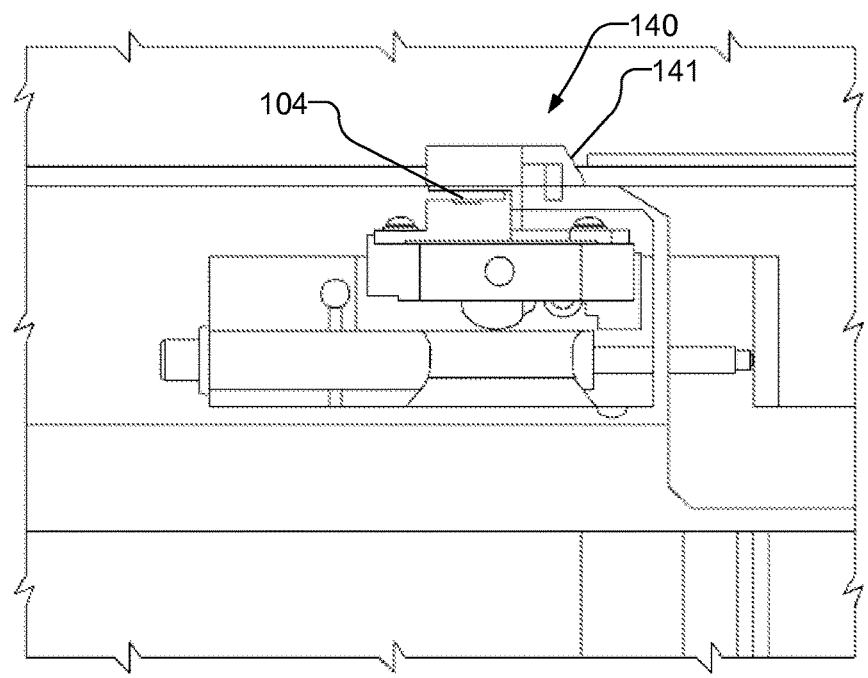
Figure 9:
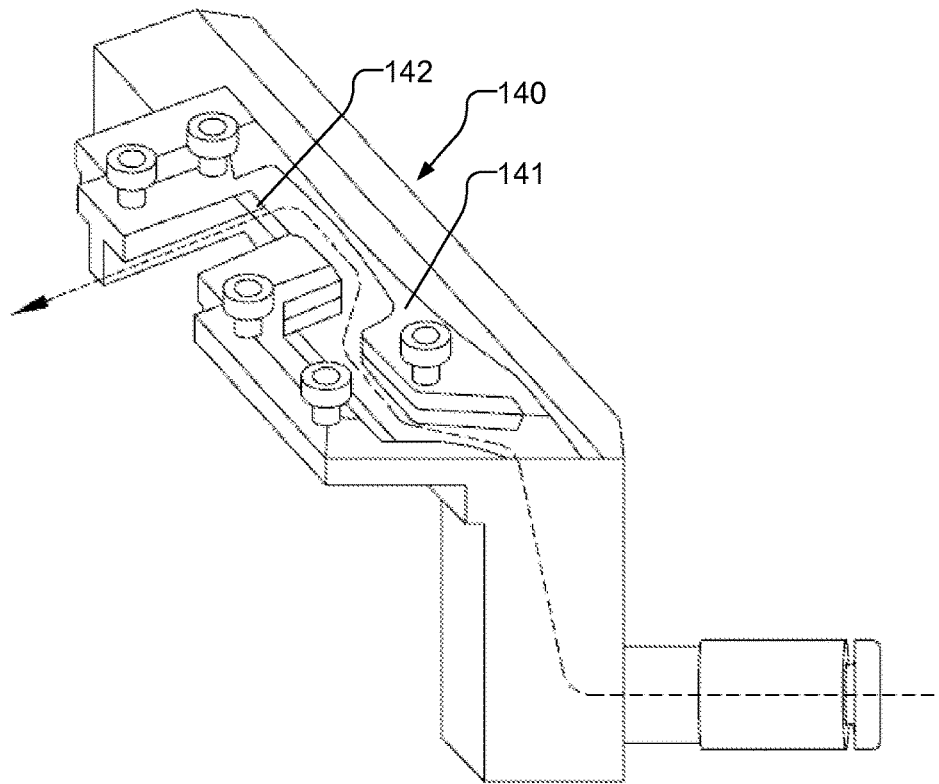
FIG. 9 is a perspective view of the purge system of FIG. 7.
Figure 10:
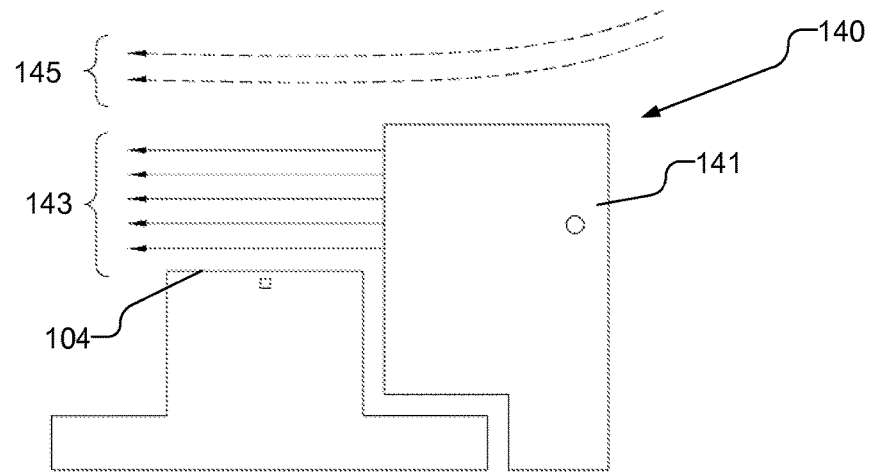
FIG. 10 illustrates the airflow from the purge system shown in FIG. 7.

FIG. 7 illustrates a side perspective view of the reference chip 104 and a purge system 140 that may be used with the IM module 100 shown in FIGS. 2 and 3, in place of or in addition to purge system 102. The purge system 140 includes a nozzle 141 that is coupled to the wafer chuck 108 so that it moves with the wafer chuck 108 and reference chip 104. FIG. 8 is a side view of the reference chip 104 and the purge system 140 and FIG. 9 is a perspective view of the purge system 140. Similar to the purge system 120, the purge system 140 is a moving nozzle system where the nozzle 141 includes at least one aperture that expels a flow of purge gas or air that is directed over the reference chip 104. As illustrated in FIG. 7, a flexible tube 144, which may be, e.g., 4 mm, may be routed to the nozzle 141 through an existing dynamic service loop and routed under the wafer 109, but not touching the wafer 109. As illustrated in FIGS. 7, 8, and 9, the nozzle 141 includes a cut-out 142 that closely conforms to the shape of the reference chip 104. By closely conforming to the shape of the reference chip 104, the purge system 140 has the advantage of allowing better control of the air flow near the reference chip 104. The designed airflow from purge system 140 is illustrated in FIG. 10, where the clean purge gas is illustrated with arrows 143 and the contaminated air flow is illustrated with arrows 145.

Purge system 140 provides clean purge gas that is directed into a flow with uniform velocity from top to bottom and into and out of the page. By way of example, the air may be set to 43 psi, or other appropriate pressure so as to achieve a 2 m/s air speed and a 2 mm thick layer of air flow. This prevents the occurrence of hot spots, i.e., areas where contamination may occur, which may be present if individual purge nozzles are used. It is desirable that the clean purge gas be directed to form a laminar flow, which is generally defined as a flow with Reynold's number below ~2000. Laminar flows have the advantage of low mixing in directions perpendicular to the flow. It is also desirable for the flow velocity to be approximately equal to the velocity of the contaminated air. This reduces the mixing between the air flows at their interface above the reference chip, in which case, the process remnants may still travel towards the reference chip by diffusion. In one embodiment, the velocity of the flow of the clean purge gas is set such that the clean purge gas blows the process remnants across the reference chip 104 faster than the process remnants can diffuse through the layer of the clean purge gas to the surface of the reference chip 104.

Figure 11:
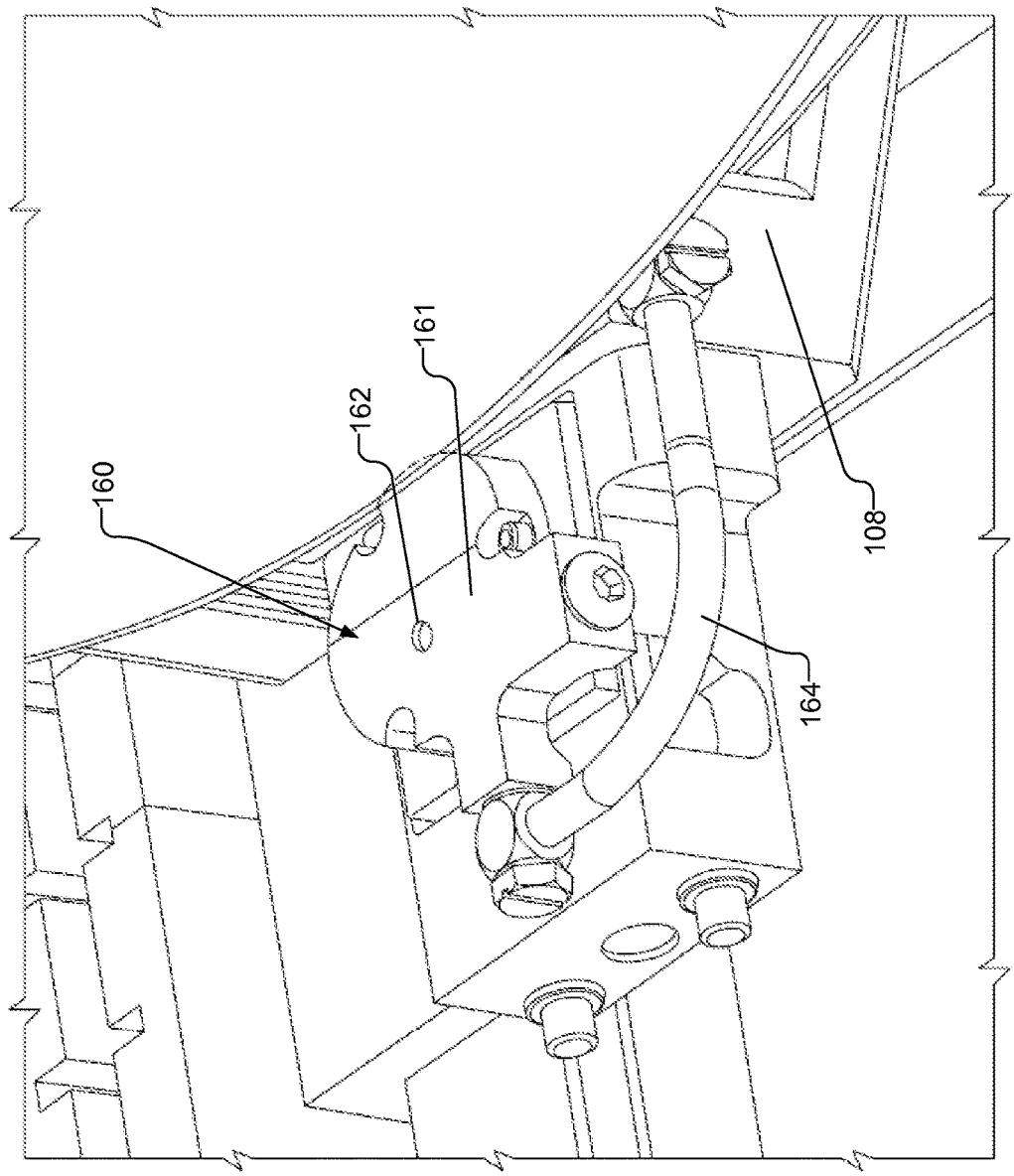
FIGS. 11, 12, and 13 illustrate a perspective view, top view, and side cross-sectional view, respectively, of a purge system that encloses a reference chip.
Figure 12:
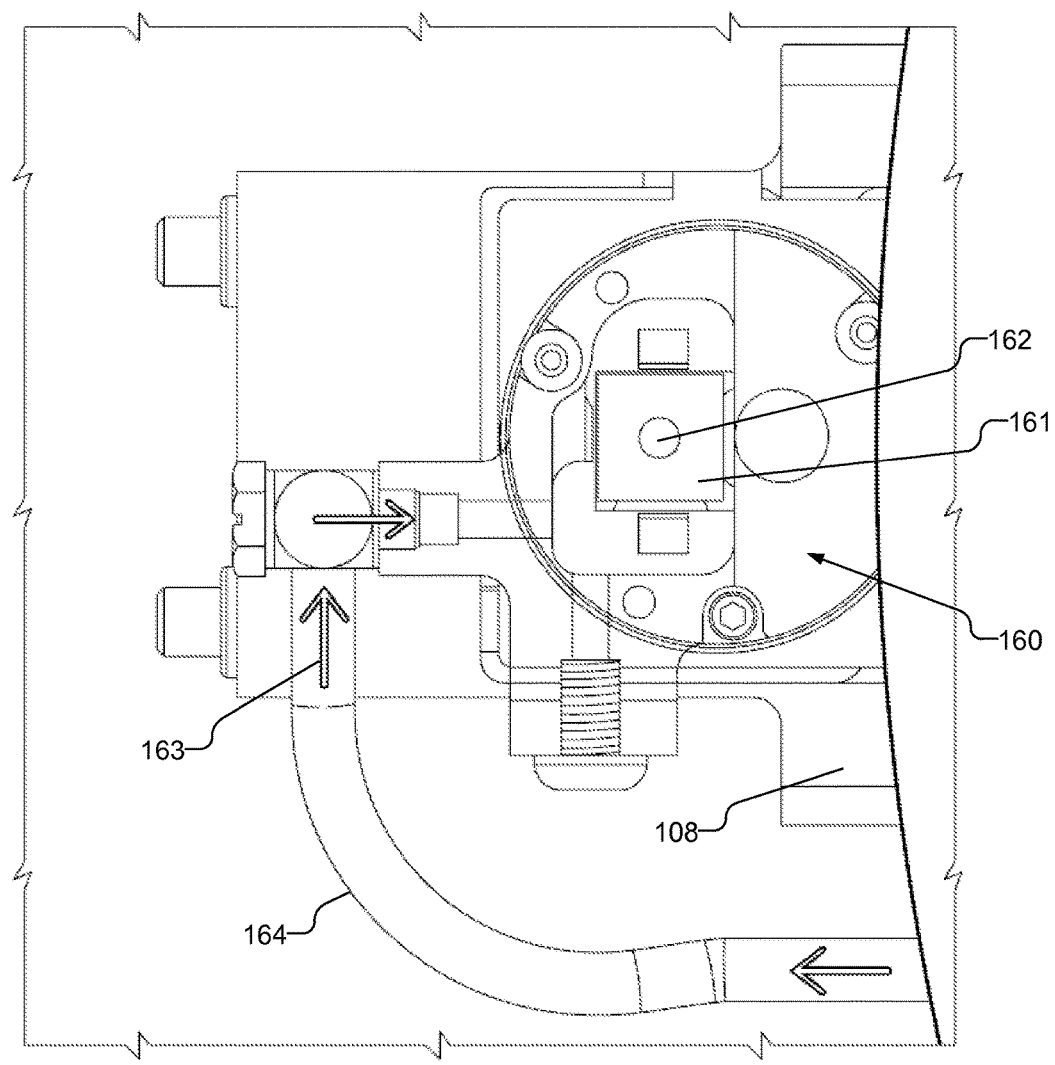
Figure 13:
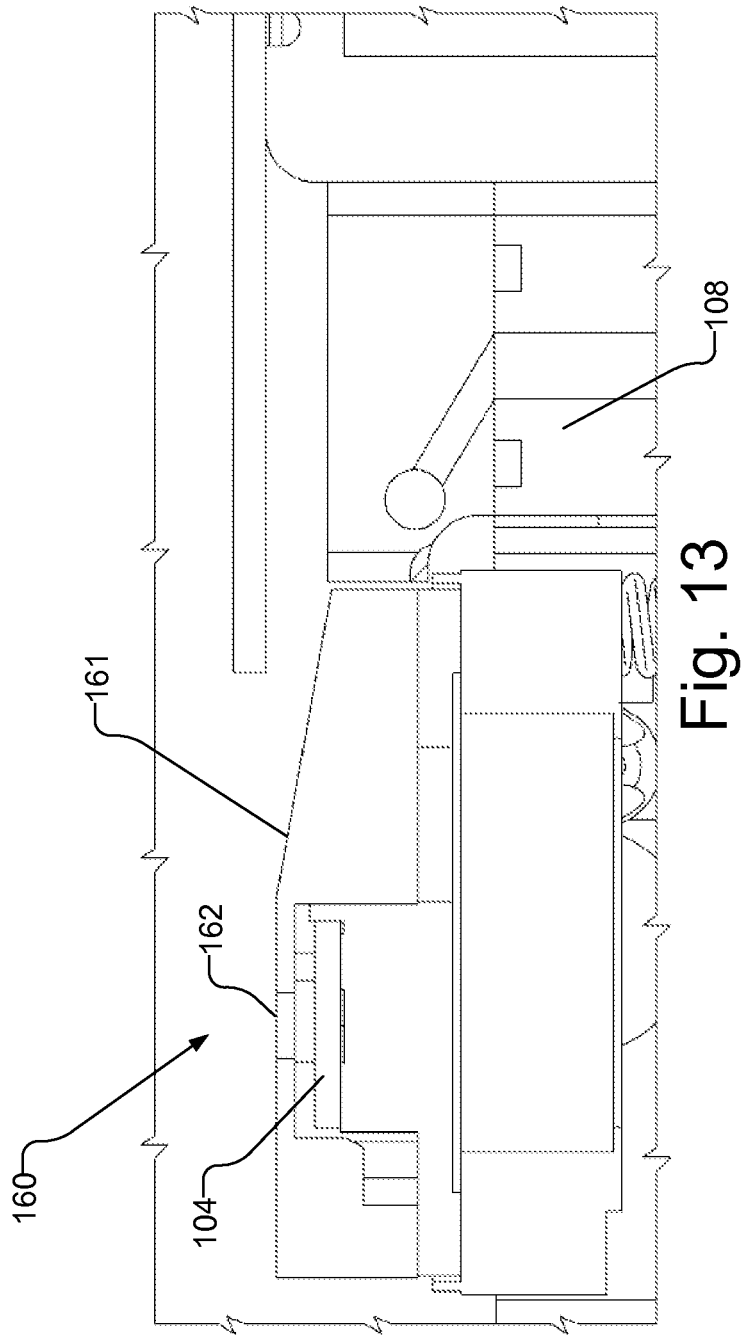

FIG. 11 illustrates a perspective view of a purge system 160 that includes an enclosure 161 that encloses the reference chip 104 that may be used with the IM module 100 shown in FIGS. 2 and 3, in place of or in addition to purge system 102. FIG. 12 is a top view of the purge system 160 and FIG. 13 is a side cross-sectional view of the purge system 160. Similar to purge systems 120 and 140, purge system 160 is coupled to the wafer chuck 108 so that it moves with the wafer chuck 108 and reference chip 104 to various positions. The enclosure 161 of the purge system 160 surrounds the reference chip 104 and includes at least one aperture that expels purge gas or air that is directed over the reference chip 104 and an exit aperture 162 through which purge gas or air exits the enclosure 161 and through which the metrology device can sample the reference chip 104. A flexible air connection 164 is coupled to the enclosure 161 to provide a positive air pressure within the enclosure 161 to prevent the process remnant from entering aperture 162 and coming in contact with the reference chip 104. The airflow of the purge system 160 is illustrated in FIG. 11 with arrows 143.

Figure 14:
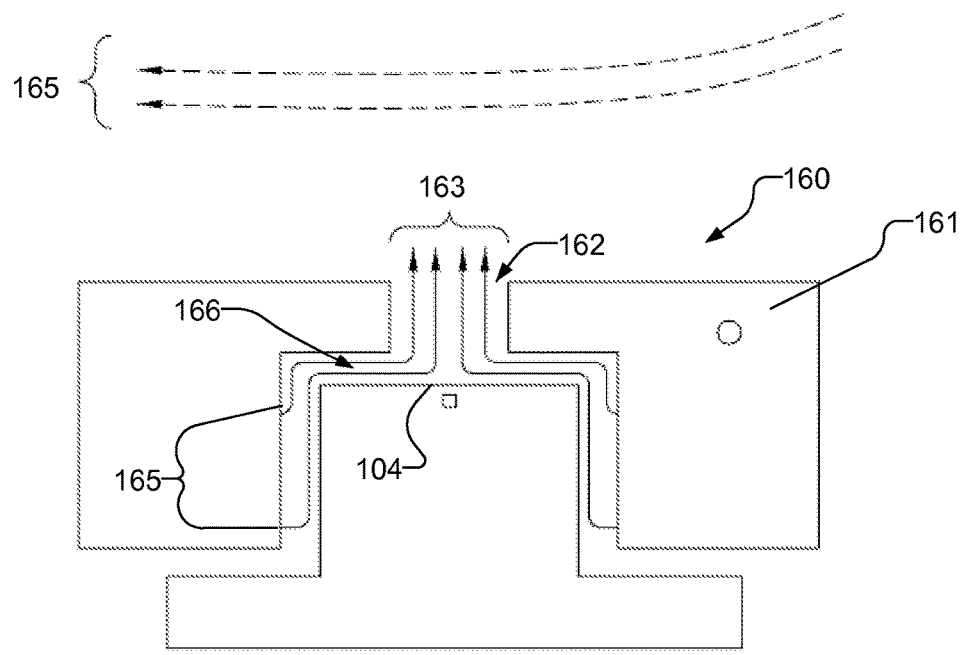
FIG. 14 illustrates the airflow from the purge system shown in FIG. 11.

The designed airflow from purge system 160 is illustrated in FIG. 14, where the clean purge gas is illustrated with arrows 163 and the contaminated air flow is illustrated with arrows 165. In the purge system 160, the purge air enters a chamber 166 in the enclosure 161 of the purge system 160 through at least one aperture 165, e.g., a plurality of apertures may be present on all sides of the reference chip 104, then flows out through the exit aperture 162 above the reference chip 104. The exit aperture 162 provides a clear optical path to the reference chip 104 for the optical metrology device in the IM module 100. The flow of purge gas is designed to completely fill the chamber 166 and exit through the exit aperture 162 to push contaminated air away 165 from the exit aperture 162 and prevent the flow of contaminated air 165 into the exit aperture 162. The velocity of the clean purge gas in purge system 160 directly opposes the diffusion velocity of the process remnants towards the reference chip 104. Thus, it is desirable for the air flow velocity of the purge gas through exit aperture 162 to be greater than the diffusion velocity.

Figure 15:
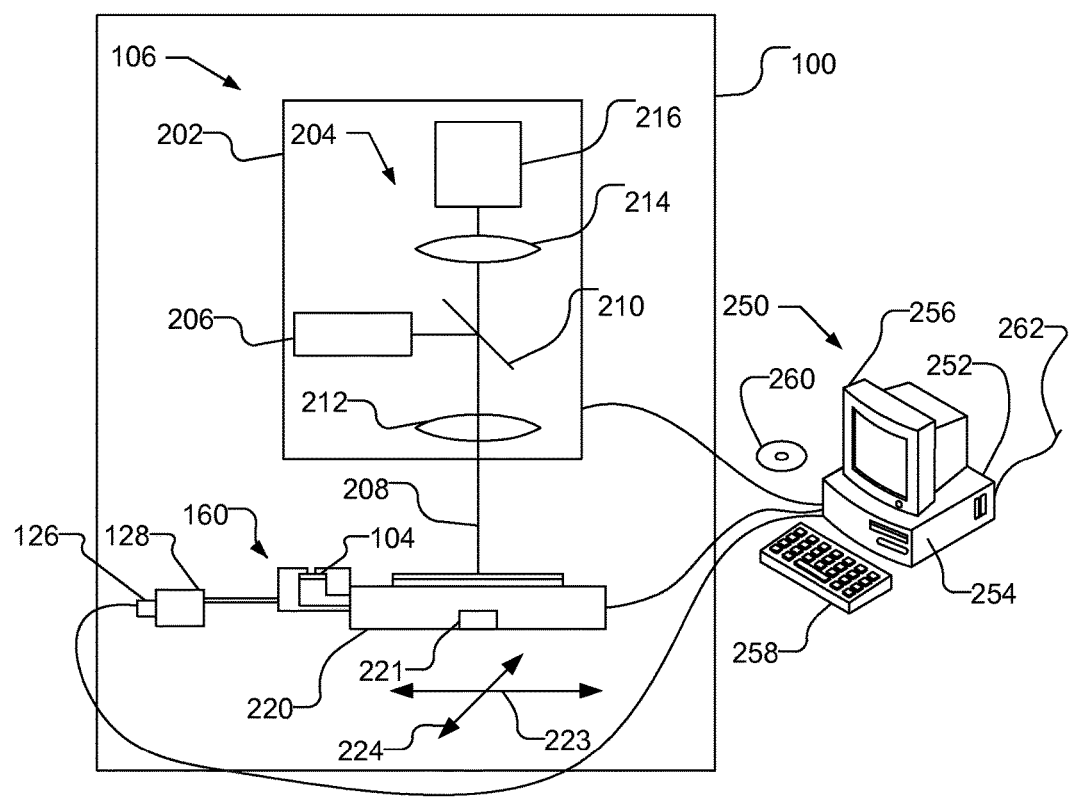
FIG. 15 is a schematic view of a metrology device that may be used in the integrated metrology module.

FIG. 15 is a schematic view of the integrated metrology module 100 with the metrology device 106 and illustrating a purge system, such as purge system 160 for the sake of example. Metrology device 106 includes an optical head 202 coupled to a computer 250, such as a workstation, a personal computer, central processing unit or other adequate computer system, or multiple systems. The optical metrology device 200 illustrated in FIG. 15 is, e.g., a spectroscopic reflectometer. If desired, other metrology devices, including single wavelength or spectroscopic devices, may be used with the IM module 100 and purge devices described herein, such as ellipsometers, scatterometers, interometers, microscopes, and others. Additionally, if desired, multiple optical heads, i.e., different metrology devices, may be combined in the same metrology device 106. The computer 250 may also control the movement of a chuck 220 that holds the wafer 230 via actuators 221 and additionally or alternatively at least a portion of the metrology device 106 to place a desired region of the wafer or reference chip in the optical path of the metrology device 106. For example, the chuck 220 may be capable of, e.g., Polar (i.e., R and θ) coordinates or Cartesian coordinates (as illustrated by arrows 223 and 224), if there is room in the IM module 100. The chuck 220 and/or optical head 202 may also be capable of vertical motion, e.g., for focusing.

The optical head 202 may include an optical system 204 including a broadband light source 206, such as a Xenon Arc lamp and/or a Deuterium lamp, and a detector 216, such as a spectrometer. In operation, light produced by the light source 206 may be directed toward the sample 230 (or reference chip 104), along optical axis 208 with a beam splitter 210. An objective 212, which may be at least part of the optics 1061, shown in FIGS. 2 and 3, focuses the light onto the sample 230 and receives reflected light from the sample 230. The reflective light may pass through the beam splitter 210 and is focused with lens 214 onto the detector 216. The detector 216 provides a spectroscopic signal to the computer 250. The objective 212, beam splitter 210, lens 214, and detector 216 are merely illustrative of typical optical elements that may be used. Additional optical elements, such as a polarizer and/or analyzer, may be used if desired. Moreover, generally, additional optical elements such as field stops, lenses, etc. may be present in the optical system 204.

The computer 250 includes a processor 252 with memory 254, as well as a user interface including e.g., a display 256 and input devices 258. The computer 250 may be coupled to control any of the purge devices described herein, such as purge system 160, using a flow controller 126, which may be coupled to a gas supply 128 or the purge device to control the flow of air or gas. Additionally, non-transitory computer-usable storage medium 260 may have computer-readable program code embodied thereon and may be used by the computer 250 for causing the processor to control the metrology device and to perform the functions described herein., including controlling the air flow of the purge device, e.g., via the flow controller 126. The data structures and software code for automatically implementing one or more acts described in this detailed description can be implemented by one of ordinary skill in the art in light of the present disclosure and stored, e.g., on a computer readable storage medium 260, which may be any device or medium that can store code and/or data for use by a computer system such as processor 252. The computer-usable storage medium 260 may be, but is not limited to, magnetic and optical storage devices such as disk drives, magnetic tape, compact discs, and DVDs (digital versatile discs or digital video discs). A communication port 262 may also be used to receive instructions that are stored in memory 254 or other storage in computer 250 and used to program the computer 250 to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. An apparatus comprising:
a chuck for holding a sample and positioning the sample with respect to an optical metrology device;
a reference chip for the optical metrology device, the reference chip being movable to various positions with respect to the optical metrology device, wherein one of the various positions is within an optical path of the optical metrology device when the reference chip is measured by the optical metrology device for calibration and another of the various positions is not within the optical path of the optical metrology device while the optical metrology device is measuring the sample held on the chuck; and
a reference chip purge device that provides a flow of purge gas or air that is directed to the reference chip while the reference chip is in the various positions.

2. The apparatus of claim 1, wherein the reference chip is mounted to the chuck and is movable to the various positions with respect to the optical metrology device by movement of the chuck.

3. The apparatus of claim 1, wherein the chuck moves with Polar coordinates, the reference chip is mounted to the chuck and has a linear direction of travel between the various positions, wherein the reference chip purge device does not move with respect to the optical metrology device and is aligned with the linear direction of travel of the reference chip to provide the flow of the purge gas or air directed to the reference chip while the reference chip is in the various positions.

4. The apparatus of claim 3, wherein the reference chip purge device comprises a linear purge tube having a plurality of apertures through which the purge gas or air is directed over the reference chip while the reference chip is moved in a linear direction.

5. The apparatus of claim 4, wherein the reference chip purge device further comprises a pair of tubes coupled to the linear purge tube and are located to sides of the optical path of the optical metrology device so as to not obstruct the optical path of the optical metrology device, the pair of tubes having a second plurality of apertures through which the purge gas or air is directed over the reference chip while the reference chip is positioned in the optical path of the optical metrology device.

6. The apparatus of claim 5, wherein the pair of tubes have a third plurality of apertures through which the purge gas or air is directed over a window or lens of the optical metrology device.

7. The apparatus of claim 1, wherein the reference chip and the reference chip purge device are coupled to the chuck and are together movable to the various positions with respect to the optical metrology device by movement of the chuck.

8. The apparatus of claim 7, wherein the reference chip purge device comprises a nozzle that at least partially surrounds the reference chip, the nozzle comprising at least one aperture that directs the purge gas or air over the reference chip.

9. The apparatus of claim 7, wherein the reference chip purge device comprises an enclosure around the reference chip, the enclosure comprising at least one aperture that directs the purge gas or air over the reference chip and an exit aperture through which the purge gas or air exits the enclosure and through which the optical metrology device samples the reference chip.

10. The apparatus of claim 1, wherein the apparatus is an integrated metrology module.

11. An integrated metrology module comprising:
a chuck for holding a sample and moving the sample in a linear direction to position the sample with respect to an optical metrology device;
a reference chip for the optical metrology device, the reference chip being mounted to the chuck and movable in the linear direction to various positions with respect to the optical metrology device; and
a reference chip purge device comprising a linear purge tube aligned in the linear direction and having a plurality of apertures through which purge gas or air is directed over the reference chip while the reference chip is moved in the linear direction.

12. The integrated metrology module of claim 11, wherein the reference chip purge device further comprises a pair of tubes coupled to the linear purge tube that are located to sides of an optical path of the optical metrology device so as to not obstruct the optical path of the optical metrology device, the pair of tubes having a second plurality of apertures through which the purge gas or air is directed over the reference chip while the reference chip is positioned in the optical path of the optical metrology device.

13. The integrated metrology module of claim 12, wherein the pair of tubes have a third plurality of apertures through which the purge gas or air is directed over a window or lens of the optical metrology device.

14. An integrated metrology module comprising:
a chuck for holding a sample and positioning the sample with respect to an optical metrology device;
a reference chip for the optical metrology device, the reference chip coupled to the chuck and being movable to various positions with respect to the optical metrology device by movement of the chuck; and
a reference chip purge device coupled to the chuck and movable with the reference chip to the various positions with respect to the optical metrology device by movement of the chuck, the reference chip purge device comprising at least one aperture through which purge gas or air is expelled over the reference chip while the reference chip is in the various positions.

15. The integrated metrology module of claim 14, wherein the reference chip purge device comprises a nozzle that at least partially surrounds the reference chip, the nozzle comprising the at least one aperture that directs the purge gas or air over the reference chip.

16. The integrated metrology module of claim 14, wherein the reference chip purge device comprises an enclosure around the reference chip, the enclosure comprising the at least one aperture that directs the purge gas or air over the reference chip and an exit aperture through which the purge gas or air exits the enclosure and through which the optical metrology device samples the reference chip.

* * * * *